(12) United States Patent
Schulte et al.

(10) Patent No.: US 6,716,273 B1
(45) Date of Patent: Apr. 6, 2004

(54) METHOD AND DEVICE FOR ELIMINATING OXYGEN CONTAINED IN AQUEOUS MONOMER SOLUTIONS

(75) Inventors: Juergen Schulte, Krefeld (DE); Detlef Albin, Moers (DE)

(73) Assignee: Stockhausen GmbH & Co. KG, Krefeld (DE)

( * ) Notice: Subject to any disclaimer, the term of this patent is extended or adjusted under 35 U.S.C. 154(b) by 0 days.

(21) Appl. No.: 10/048,984

(22) PCT Filed: Aug. 2, 2000

(86) PCT No.: PCT/EP00/07475

§ 371 (c)(1),
(2), (4) Date: Feb. 19, 2002

(87) PCT Pub. No.: WO01/12291

PCT Pub. Date: Feb. 22, 2001

(30) Foreign Application Priority Data

Aug. 17, 1999 (DE) .......................... 199 38 574

(51) Int. Cl.[7] .............................................. B01D 19/00
(52) U.S. Cl. .............................. 95/260; 95/263; 95/265; 96/202; 96/217
(58) Field of Search .................... 95/263, 265, 260; 96/217, 202, 203; 210/185; 578/301, 483

(56) References Cited

U.S. PATENT DOCUMENTS

| | | | |
|---|---|---|---|
| 2,274,658 A | * | 3/1942 | Booth |
| 2,294,827 A | * | 9/1942 | Booth |
| 3,229,449 A | * | 1/1966 | Hogue |
| 4,332,933 A | * | 6/1982 | Di Drusco et al. |
| 4,372,758 A | * | 2/1983 | Bobst et al. |
| 4,758,654 A | * | 7/1988 | Brod et al. |
| 5,292,863 A | * | 3/1994 | Wang |
| 5,409,523 A | * | 4/1995 | Haeuser |
| 5,591,252 A | * | 1/1997 | Haeuser |
| 5,688,910 A | * | 11/1997 | Wang |
| 5,799,412 A | * | 9/1998 | Yamamoto et al. |
| 6,345,908 B1 | * | 2/2002 | Gmeiner |
| 2002/0017193 A1 | * | 2/2002 | Ramos |

FOREIGN PATENT DOCUMENTS

| | | | |
|---|---|---|---|
| DE | 35 40 994 | | 5/1986 |
| EP | 0 185 827 | | 7/1986 |
| EP | 0 646 400 | | 4/1995 |
| JP | 62-089908 | | 4/1987 |
| JP | 02-006413 | * | 1/1990 |

* cited by examiner

Primary Examiner—Duane S. Smith
(74) Attorney, Agent, or Firm—Oblon, Spivak, McClelland, Maier & Neustadt, P.C.

(57) ABSTRACT

A continuous process for removing oxygen from aqueous monomer solutions, including flowing an inert gas and a monomer solution in a column-shaped apparatus as a countercurrent, wherein the monomer solution is added at the head of the apparatus, flows through the apparatus as a liquid column, and is withdrawn slightly above the bottom, at least one section of the liquid column is mixed in radial flow direction and in a turbulent fashion, and the at least one section of the liquid column is mixed using at least one stirring element which is one of a turbine disk and a dispersing disk.

20 Claims, 2 Drawing Sheets

METHOD AND DEVICE FOR ELIMINATING OXYGEN CONTAINED IN AQUEOUS MONOMER SOLUTIONS

BACKGROUND OF THE INVENTION

1. Field of the Invention

The present invention relates to a method and device for eliminating oxygen contained in aqueous monomer solutions.

2. Description of Background Art

Oxygen inhibits and affects the polymerization of monomers and also, in particular, the free-radical polymerization of water-soluble monomers in the production of water-soluble or water-swellable polymer products used inter alia as flocculants, dehydration or retention agents, or as superabsorbers or thickening agents.

Extensive removal of oxygen prior to and during polymerization prevents inhibition or termination of the polymerization reaction and, particularly in industrial production processes, enables controlled induction and progress thereof and thus, the manufacture of the desired polymer products.

Therefore, the past has seen numerous attempts of providing processes and/or devices by means of which oxygen is removed from the monomer solutions. As a rule, these processes are based on stripping the oxygen from the monomer solution using an inert gas. Thus, for example, DE 35 40 994 teaches intimate mixing of the monomer solution with nitrogen in a two-fluid nozzle, thereby removing the oxygen from the monomer solution. However, this procedure is disadvantageous in that the nozzle tends to become blocked and/or sticky as a result of polymer formation, so that oxygen removal is liable to give trouble. Moreover, long downtimes constantly occur as a result of necessary maintenance and, in addition, the consumption of inert gas in this process is comparatively high.

SUMMARY OF THE INVENTION

It is therefore the object of the present invention to provide a process for removing oxygen from monomer solutions, which process has low susceptibility to failure and a very low specific consumption of inert gas and permits continuous operation.

According to the invention, the object is accomplished by providing a continuous process for removing oxygen from monomer solutions using an inert gas in a column-shaped apparatus.

Preferably, the apparatus is a cylindrical container, the diameter to height ratio of which being from 0.95 to 0.1, preferably from 0.8 to 0.3, and more preferably from 0.5 to 0.35.

The inert gas preferably is dispersed at the bottom of the apparatus, advantageously in the form of fine bubbles, introduced, and withdrawn at the head of the apparatus. Dispersion of the inert gas preferably is effected using a membrane or a pipe socket. Preferred inert gases are nitrogen and/or carbon dioxide. The monomer solution preferably is added at the head of the apparatus, flows through the apparatus as a liquid column, and preferably is withdrawn slightly above the bottom. The residence time of the liquid in the apparatus is varied by means of the filling level and flow rate.

In a preferred embodiment, at least one section of the liquid column is subjected to mixing. Preferably, multiple sections of the liquid column are subjected to mixing. The height of each section preferably is from 5 to 50%, more preferably from 10 to 30% of the liquid column overall height. In case of two sections; the height of the upper section preferably is from 5 to 50%, more preferably from 10 to 30%, and the height of the lower section preferably from 10 to 30% of the liquid column overall height. Preferably, said mixing extends across the entire cross-section of the liquid column. Said mixing advantageously is effected in a turbulent fashion. It is particularly advantageous to perform said mixing using stirring elements, preferably turbine agitators and/or dispersing disks. It is particularly preferred that each one section is mixed by two turbine agitators, two dispersing disks, or by one turbine agitator and one dispersing disk, the dispersing disk preferably being arranged below the turbine agitator. Thereby, the radial stirring effects, i.e., the radial flow directions are utilized by these stirring elements.

The height of the sections depends on the type of aqueous monomer solution. When producing polyelectrolytes containing cationic monomers, the height is selected to be higher. Multiple sections can be arranged in parallel or in series.

The process of the invention is advantageous in that the specific consumption of inert gas for complete removal of oxygen is exceedingly low. By varying the filling level and flow rate, it is possible to render the most diverse monomer solutions completely free of oxygen. The downtimes due to maintenance are very short in the process of the invention, and the time intervals between maintenance operations are longer.

Another object of the present invention is to provide an apparatus in which the process of the invention can be performed with particular advantage and which is easy to clean and to maintain.

According to the invention, said object is accomplished by providing an apparatus which can be filled at least in part with a liquid column and which has

- a gas inlet, preferably a gas dispersing means, and a gas outlet,
- a liquid inlet and a liquid outlet, and
- at least one means used to mix a section of the liquid column, preferably in a turbulent fashion.

Preferably, the apparatus is cylindrical and has a diameter to height ratio of from 0.95 to 0.1, preferably from 0.8 to 0.3, and more preferably from 0.5 to 0.35.

In a preferred embodiment, the gas dispersing means is arranged at the bottom of the apparatus. Gas dispersion preferably is performed through a membrane or a pipe socket.

Preferably, the means for mixing is a stirring element. In a preferred embodiment, the stirring element is a turbine agitator and/or a dispersing disk. In a particularly preferred fashion, the stirring element consists of two turbine agitators, two dispersing disks, or one turbine agitator and one dispersing disk, the turbine agitator preferably being arranged above the dispersing disk. The stirring element is arranged on a shaft driven by a motor which preferably is situated at the head of the apparatus. Using said stirring element, the liquid column is subjected to locally limited mixing, preferably in a turbulent fashion. Advantageously, 5–50%, preferably 10–30% of the overall height of the liquid column and preferably the entire cross-section thereof is mixed by each stirring element. The apparatus according to the invention preferably has multiple stirring elements, more preferably two stirring elements; preferably 5–50%, more preferably 10–30% of the overall height of the liquid column is mixed by the upper one, and preferably 10–30% by the lower one.

In a preferred embodiment, the apparatus according to the invention additionally has internal members preferably designed in a disk shape and extending across part of the cross-section of the apparatus so as to avoid back-mixing of the liquid column as much as possible. These internal members preferably are of annular shape and preferably arranged above the stirring elements.

The apparatus preferably has an automatic filling level control, by means of which the height of the liquid column is maintained at a specific level.

The apparatus according to the invention preferably is used to remove oxygen from a monomer solution. In this event, an oxygen measuring means preferably is arranged in the outlet of the apparatus, which is used to monitor the oxygen content and optionally can be employed in the automatic control of oxygen removal. If the measured oxygen content is too high, the filling level of the container is increased and/or the flow rate is reduced. In the event of an excessively high oxygen concentration, it is also possible to increase the flow of the inert gas volume.

The apparatus of the invention may also be used in flotation and in any type of mass transfer and/or reaction process.

The apparatus according to the invention is readily produced, easy to maintain, and has little susceptibility to failure. When used according to the process of the invention, the service time, i.e., the time interval between two maintenance operations is exceedingly long compared to the use of other apparatus for such purposes. At the same time, the specific consumption of nitrogen is lower compared to apparatus according to prior art. Multiple apparatus can be arranged in parallel or in series. In a highly flexible fashion, the apparatus can also be employed for most various purposes and provided with specific gas dispersing means and/or internal members to this end. The apparatus according to the invention can be used in continuous or batch processes. In case of production intermissions, for example, the monomer solution in the apparatus can be restabilized by gassing with air and put to safe storage. A short time before restarting, the monomer solution again is made free of oxygen using inert gas.

With reference to two examples, the apparatus of the invention will be illustrated hereinbelow. The explications are merely by way of example and are thus not limiting to the general idea of the invention.

DETAILED DESCRIPTION OF THE EMBODIMENTS

Figure 1:
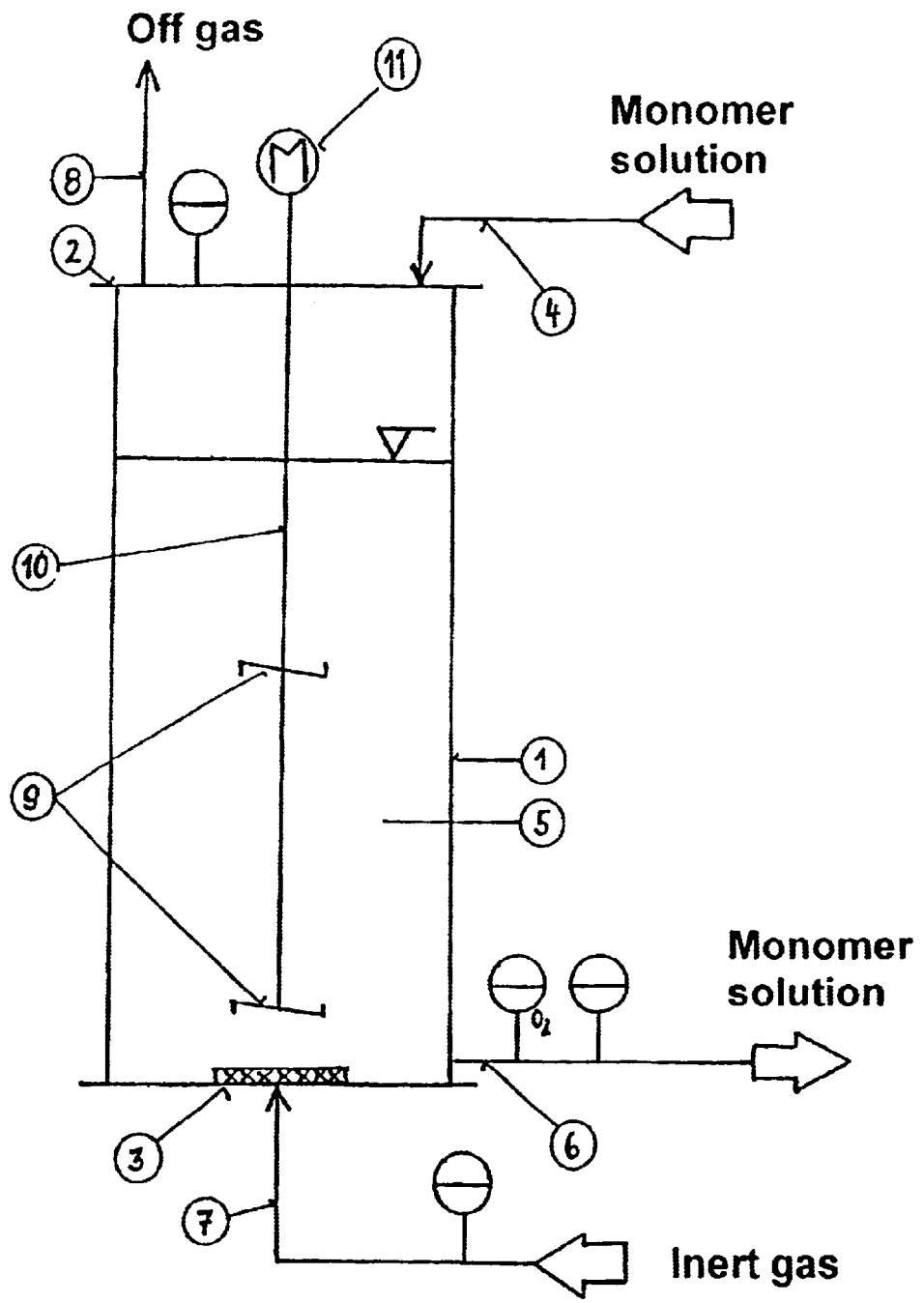
FIG. 1 schematically illustrates the apparatus according to the invention—with no internal members—for removing oxygen from monomer solutions.

FIG. 1 illustrates the apparatus 1 of the invention with no internal members. The apparatus is of cylindrical shape and has a cap 2 at its head and a cap 3 at its bottom wherein a membrane is inserted. A monomer solution is pumped into the apparatus through inlet 4 in cap 2 and flows through the apparatus in the form of a liquid column 5, before discharging from the apparatus of the invention through outlet 6 situated slightly above the bottom. About 80% of the apparatus is filled with monomer solution.

The stream of inert gas 7 is conducted as a countercurrent to the stream of liquid. To this end, the stream of inert gas, dispersed in the form of fine bubbles, is introduced into the apparatus through the membrane in cap 3, flows through the liquid column 5, and discharges from the apparatus 1 via outlet 8. Those skilled in the art will recognize that inert gas dispersion may also be effected by means of any other dispersing element known in the art, such as nozzle or a frit or the like.

In the apparatus, two stirring elements 9 are arranged on a stirring shaft 10 driven by a motor 11 mounted on cap 2. Only within the range around the turbine disks, the monomer solution is subjected to turbulent mixing by the stirring elements, said mixing extending across the entire cross-section of the apparatus. From 20 to 50% of the overall height of the liquid column is turbulently mixed by the stirring elements.

The apparatus of the invention has a filling level measuring and controlling means which is used to adjust any desired filling level in the apparatus. Furthermore, the apparatus has an oxygen measuring means in its lower outlet, which is used to measure the oxygen content of the monomer solution and to control oxygen removal accordingly.

Figure 2:
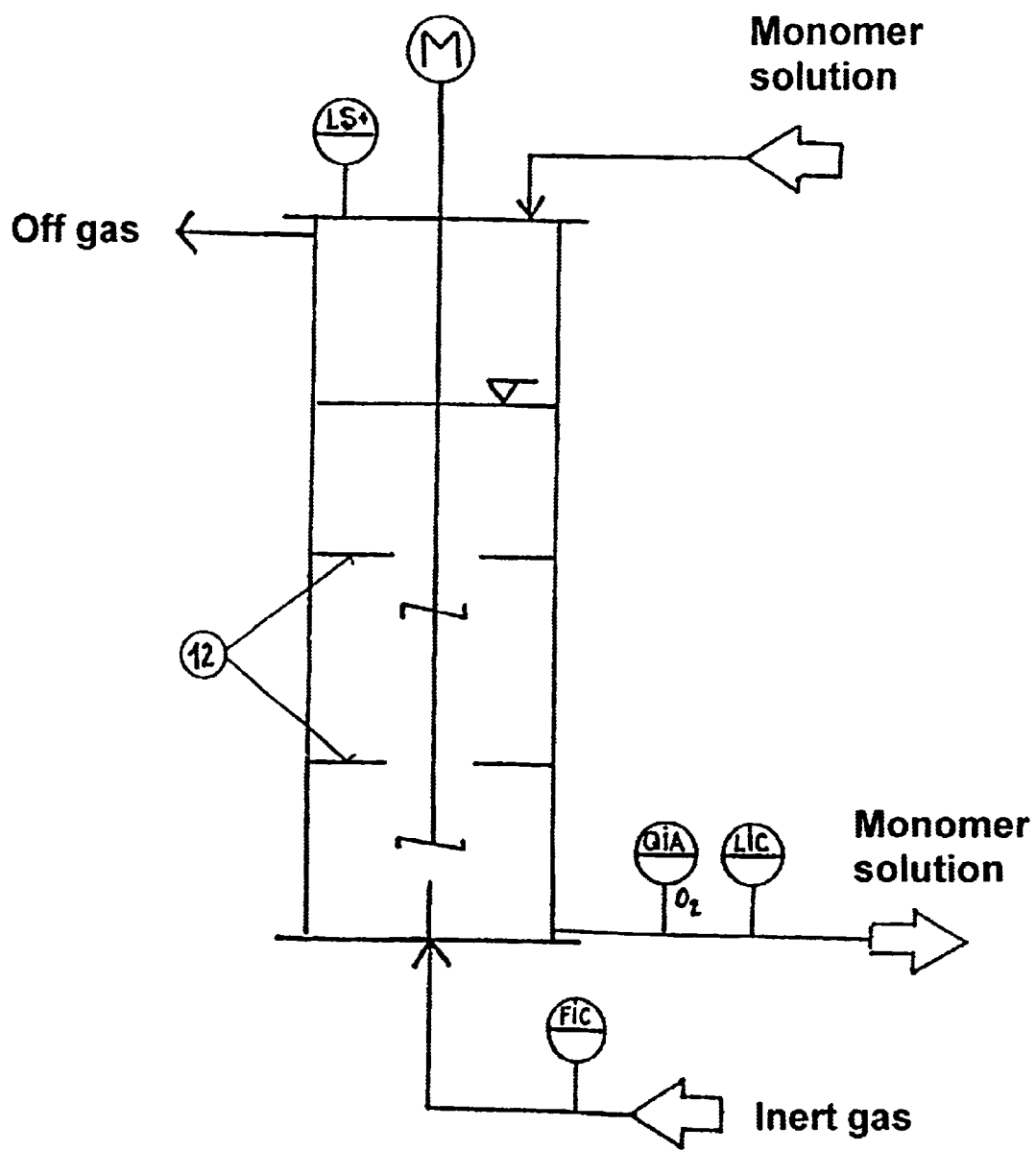
FIG. 2 schematically illustrates the apparatus according to the invention—including internal members—for removing oxygen from monomer solutions.

FIG. 2 shows the apparatus according to FIG. 1, which in this case has internal members 12 having annular shape and being arranged slightly above the turbine disks. The stream of inert gas is introduced via a pipe socket.

What is claimed is:

1. A continuous process for removing oxygen from aqueous monomer solutions, comprising flowing an inert gas and a monomer solution in a column-shaped apparatus as a countercurrent, wherein the monomer solution is added at the head of the apparatus, flows through the apparatus as a liquid column, and is withdrawn slightly above the bottom, at least one section of the liquid column is mixed in radial flow direction and in a turbulent fashion, and the at least one section of the liquid column is mixed using at least one stirring element which is one of a turbine disk and a dispersing disk.

2. The process according to claim 1, wherein the inert gas is introduced at the bottom of the apparatus and withdrawn at the head thereof.

3. The process according to claim 2, wherein the inert gas is dispersed using a membrane and/or at least one pipe socket.

4. The process according to claim 1, wherein the inert gas is nitrogen and/or carbon dioxide.

5. An apparatus configured to be filled at least in part with a liquid column, comprising:
a gas inlet, and a gas outlet,
a liquid inlet and a liquid outlet, and
mixing means for mixing a section of the liquid column wherein the mixing means comprises at least one stirring element.

6. The apparatus according to claim 5, further comprising gas dispersing means for dispersing a gas, the gas dispersing means being situated at the bottom of the apparatus and comprising a membrane and/or at least one pipe socket.

7. The apparatus according to claim 5, wherein the at least one stirring element comprises at least one turbine agitator and at least one dispersing disk.

8. An apparatus configured to be filled at least in part with a liquid column, comprising:
a gas inlet, and a gas outlet;
a liquid inlet and a liquid outlet;
mixing means for mixing a section of the liquid column, the mixing means comprising at least one stirring element; and a plurality of internal members arranged above the at least one stirring element.

9. An apparatus configured to be filled at least in part with a liquid column, comprising:

a cylindrical body;

a gas inlet and a gas outlet;

a liquid inlet and a liquid outlet;

mixing means for mixing a section of the liquid column, the mixing means comprising at least one stirring element; and a plurality of internal members positioned above the at least one stirring element and having an annular shape.

10. The apparatus according to claim 9, wherein the diameter to height ratio of the apparatus is from 0.95 to 0.1.

11. The apparatus according to claim 9, wherein the diameter to height ratio of the apparatus is from 0.8 to 0.3.

12. The apparatus according to claim 9, wherein the diameter to height ratio of the apparatus is from 0.5 to 0.35.

13. The apparatus according to claim 5, further comprising gas dispersing means for dispersing a gas.

14. The apparatus according to claim 5, wherein the mixing means mixes in a turbulent fashion.

15. The apparatus according to claim 8, wherein the mixing means mixes in a turbulent fashion.

16. The apparatus according to claim 8, further comprising gas dispersing means for dispersing a gas.

17. The apparatus according to claim 16, wherein the gas dispersing means is situated at the bottom of the apparatus and comprises a membrane and/or at least one pipe socket.

18. The apparatus according to claim 9, wherein the mixing means mixes in a turbulent fashion.

19. The apparatus according to claim 9, further comprising gas dispersing means for dispersing a gas.

20. The apparatus according to claim 19, wherein the gas dispersing means is situated at the bottom of the apparatus and comprises a membrane and/or at least one pipe socket.

* * * * *

(12) EX PARTE REEXAMINATION CERTIFICATE (5584th)
United States Patent
Schulte et al.

(10) Number: US 6,716,273 C1
(45) Certificate Issued: Oct. 24, 2006

(54) METHOD AND DEVICE FOR ELIMINATING OXYGEN CONTAINED IN AQUEOUS MONOMER SOLUTIONS

(75) Inventors: Juergen Schulte, Krefeld (DE); Detlef Albin, Moers (DE)

(73) Assignee: Stockhausen GmbH & Co. KG, Krefeld (GB)

Reexamination Request:
No. 90/007,525, Apr. 27, 2005

Reexamination Certificate for:
Patent No.: 6,716,273
Issued: Apr. 6, 2004
Appl. No.: 10/048,984
Filed: Feb. 19, 2002

(22) PCT Filed: Aug. 2, 2000
(86) PCT No.: PCT/EP00/07475
§ 371 (c)(1),
(2), (4) Date: Feb. 19, 2002
(87) PCT Pub. No.: WO01/12291
PCT Pub. Date: Feb. 22, 2001

(30) Foreign Application Priority Data
Aug. 17, 1999 (DE) .......................... 199 38 574

(51) Int. Cl.
*B01D 19/00* (2006.01)

(52) U.S. Cl. ............................. 95/260; 95/263; 95/265; 96/202; 96/217
(58) Field of Classification Search .................... None
See application file for complete search history.

(56) References Cited

U.S. PATENT DOCUMENTS

| 4,906,574 A | 3/1990 | Erdei et al. |
| 6,066,759 A | 5/2000 | Heider et al. |

FOREIGN PATENT DOCUMENTS

| DE | 2 300 205 | 7/1973 |
| DE | 2 930 160 C2 | 2/1981 |
| DE | 3 819 254 A1 | 12/1988 |
| DE | 195 25 474 A1 | 1/1997 |

*Primary Examiner*—Stephen Stein

(57) ABSTRACT

A continuous process for removing oxygen from aqueous monomer solutions, including flowing an inert gas and a monomer solution in a column-shaped apparatus as a countercurrent, wherein the monomer solution is added at the head of the apparatus, flows through the apparatus as a liquid column, and is withdrawn slightly above the bottom, at least one section of the liquid column is mixed in radial flow direction and in a turbulent fashion, and the at least one section of the liquid column is mixed using at least one stirring element which is one of a turbine disk and a dispersing disk.

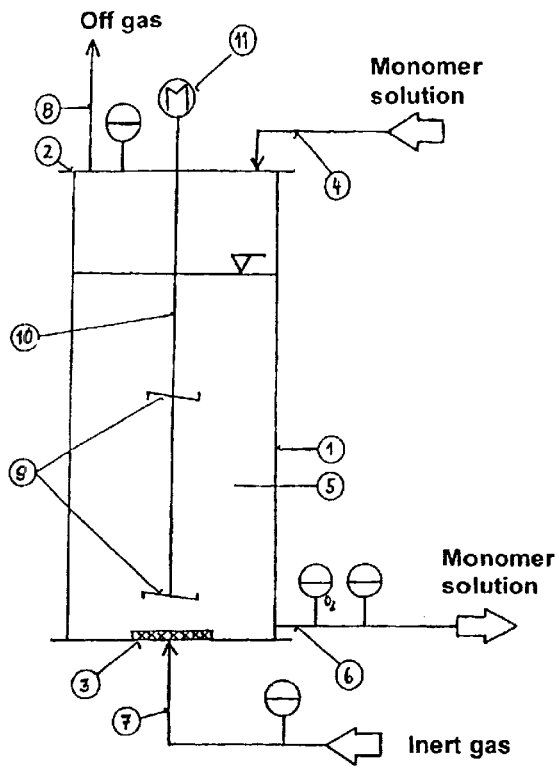

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1–4 is confirmed.

Claims 5–20 are cancelled.

\* \* \* \* \*